United States Patent [19]
Wassil

[11] Patent Number: 5,388,570
[45] Date of Patent: Feb. 14, 1995

[54] EMERGENCY CPR MASK STATION

[76] Inventor: Joseph D. Wassil, 410 S. Bethel St., Baltimore, Md. 21230

[21] Appl. No.: 161,173

[22] Filed: Dec. 3, 1993

Related U.S. Application Data

[63] Continuation of Ser. No. 878,261, May 4, 1992, abandoned.

[51] Int. Cl.⁶ ............................................. A62B 25/00
[52] U.S. Cl. ........................ 128/200.24; 128/202.28; 128/917; 220/554; 312/245
[58] Field of Search .............. 128/857, 859, 917, 918, 128/909, 203.11, 202.28, 202.26, 202.29, 207.12, 201.11, 203.21, 205.13, 200.24; 312/242, 245; 220/502, 500, 554

[56] References Cited

U.S. PATENT DOCUMENTS

| | | | |
|---|---|---|---|
| 1,178,719 | 4/1916 | Hildebrand | 340/545 X |
| 2,280,050 | 4/1942 | Alexander et al. | 128/203.11 |
| 2,683,260 | 7/1954 | Lavelle | 340/327 |
| 2,857,911 | 10/1958 | Bennett | 128/206.24 |
| 2,995,131 | 8/1961 | Elam et al. | 128/202.28 |
| 3,017,880 | 1/1962 | Brook | 128/203.11 |
| 3,042,910 | 7/1962 | Shull | 340/568 X |
| 3,057,347 | 10/1962 | McGee | 128/202.28 |
| 3,067,822 | 12/1962 | Hattenhauer | 169/51 |
| 3,124,124 | 3/1964 | Cross | 128/203.11 |
| 3,137,293 | 6/1964 | Green | 128/202.28 |
| 3,303,845 | 2/1967 | Detmer III | 128/202.28 |
| 3,625,351 | 12/1971 | Eisenberg | 206/484 |
| 3,722,733 | 3/1973 | Neumann | 220/602 |
| 3,802,428 | 4/1974 | Sherman | 128/202.28 |
| 3,856,177 | 12/1974 | Fudge | 220/602 |
| 4,015,250 | 3/1977 | Fudge | 340/568 |
| 4,018,242 | 4/1977 | Schlegel | 137/355.18 |
| 4,046,412 | 9/1977 | Lee | 272/200 |
| 4,109,985 | 8/1978 | Lieb, Jr. | 340/568 X |
| 4,155,608 | 5/1979 | Orlewicz | 312/204 |
| 4,178,783 | 12/1979 | Lee | 70/422 |
| 4,193,401 | 4/1980 | Handke | 251/342 |
| 4,226,101 | 10/1980 | Lee | 70/78 |
| 4,449,588 | 5/1984 | Benlolo et al. | 169/48 |
| 4,535,765 | 8/1985 | Paoluccio et al. | 128/203.11 |
| 4,663,621 | 5/1987 | Field | 340/825.31 |
| 4,697,587 | 10/1987 | Marinkovich | 128/203.11 |
| 4,763,732 | 8/1988 | Neal | 169/51 |
| 4,797,104 | 1/1989 | Laerdal et al. | 434/265 |
| 4,819,628 | 4/1989 | Eisenberg et al. | 128/203.11 |
| 4,856,506 | 8/1989 | Jinotti | 128/203.11 |
| 4,881,063 | 11/1989 | Fawcett | 340/693 |
| 4,928,830 | 5/1990 | Brewer | 206/570 |
| 4,944,291 | 7/1990 | Robertson, II et al. | 128/203.11 |
| 5,009,635 | 4/1991 | Scarberry | 604/27 |
| 5,016,649 | 5/1991 | Johnson | 128/859 |
| 5,020,529 | 6/1991 | Gobin | 128/202.28 |
| 5,055,052 | 10/1991 | Johnsen | 434/265 |

FOREIGN PATENT DOCUMENTS 2198958 6/1988 United Kingdom.

OTHER PUBLICATIONS

Boodman, Sandra G., "Contagion A Barrier To Mouth To Mouth", *Washington Post Health*, p. 5, Aug. 10, 1993.
Brenner, Barry E. and Jane Kauffman, "Reluctance of Internists and Medical Nurses to Perform Mouth-to-Mouth Resuscitation", *Archives of Internal Medicine*, vol. 153, pp. 1763–1769, Aug. 9, 1993.

(List continued on next page.)

*Primary Examiner*—Edgar S. Burr
*Assistant Examiner*—Eric P. Raciti
*Attorney, Agent, or Firm*—Banner, Birch, McKie & Beckett

[57] ABSTRACT

A cabinet housing CPR masks and non-sterile hypoallergenic latex gloves is mounted on a wall in a visible location. A plastic tie seal maintains the cabinet door closed. In the event of a CPR emergency, the seal is pulled, twisted and thereby broken, the door opened and the mask and gloves removed. When the door is opened, a lever switch on the cabinet automatically activates a loud piezo buzzer mounted on top of the cabinet, thereby alerting others to the emergency. The buzzer can be deenergized with a key-activated switch.

12 Claims, 5 Drawing Sheets

OTHER PUBLICATIONS

Michael, Anthony Don and James S. Forrester, "Mouth–To–Mouth Ventilation—The Dying Art", *American Journal of Emergency Medicine,* vol. 10, No. 2, pp. 156–161, Mar. 1992.

McCormack, Anne P. et al, "Disagreeable Physical Characteristics Affecting Bystander CPR", *Annals of Emergency Medicine,* vol. 88, pp. 283–285, Mar. 1989.

"What Our Readers Said About Resuscitating A Patient With Aids", *Nursing Life,* pp. 23–25, Sep.-Oct. 1986.

Ornato, Joseph P. et al, "Attitudes of BCLS Instructors About Mouth-to-Mouth Resuscitation During the AIDS Epidemic", *Annals of Emergency Medicine,* vol. 19, pp. 151–156, Feb. 1990.

Achong, M. R., Infectious hazards of mouth-to-mouth resuscitation. *American Heart Journal,* 1980, vol. 100, No. 5, pp. 759–760.

American Heart Association, Infection During CPR-Emergency Cardiac Care Committee, Risk of infection during CPR training and rescue: supplemental guidelines. *JAMA,* Nov. 17, 1989, vol. 262, No. 19, reprint.

Caccomo, A., A simple device for filtering mouth-to-mouth resuscitation. Letter to the editor. *Anesthesiology,* 1984, vol. 61, p. 638.

Cole, S. L., and Corday, E. Four-minute limit for cardiac resuscitation. *JAMA,* Aug. 11, 1956, vol. 161, No. 15, p.o. 1454–1458.

Cummins, R. O., and Eisenberg, M. S. Prehospital cardiopulmonary resuscitation. *JAMA,* Apr. 26, 1965, vol. 253, No. 16, p.o. 2408–2412.

Davies, J. N. P., Operator risk in mouth-to-mouth resuscitation. Letter to the editor. *The Lancet,* Sep. 15, 1979, vol. 2, p. 593.

Eisenberg, M. S., et al. Cardiac resuscitation in the community: importance of rapid provision and implications for program planing. *JAMA,* May 4, 1979, vol. 241, No. 18, 1905–1907.

Elam, J. O., et al. Head-tilt method of oral resuscitation. *JAMA,* Feb. 20, 1960, vol. 172, No. 8, p.o. 812–815.

Elam, J. O., et al. Artificial respiration by mouth-to-mouth method: A study of the respiratory gas exchange of paralyzed patients ventilated by operator's expired air. *The New England Journal of Medicine,* May 6, 1954, vol. 250, No. 18, p.o. 749–754.

Farizo, K. M., et al. Spectrum of diseases in persons with human immunodeficiency virus infection in the United States. *JAMA,* Apr. 1, 1992, vol. 267, No. 13, pp. 1798–1804.

Fauci, A. S., The acquired immune deficiency syndrome: The ever-broadening clinical spectrum. *JAMA,* May 6, 1983, vol. 249, No. 17, p. 2376.

Francis, D. P., Toward a comprehensive HIV prevention program for the CDC and the nation. *JAMA,* Sep. 16, 1992, vol. 268, No. 11, pp. 1444–1447.

Gerety, R. J. and Tabor, E., Newly licensed hepatitis B Vaccine: Known safety and unknown risks. *JAMA,* Feb. 11, 1983, vol. 249, No. 6, pp. 745–746.

Gordon, F., Tuberculosis control: Back to the future? *JAMA,* May 20, 1992, vol. 267, No. 19, pp. 2648–2650.

Gordon, A.S., et al., mouth-to-mouth versus manual artificial respiration for children and adults. *JAMA,* May 17, 1958, vol. 167, pp. 320–328.

Goucke, R., Mouth-to-mask ventilation—which mask! *The Medical Journal of Australia,* Mar. 3, 1986, vol. 144, p. 279.

Harrison, et al., Mouth-to-Mask ventilation: A superior method of rescue breathing. *Annals of Emergency Medicine,* Feb., 1982, vol. 11:2, pp. 74–76.

Heilman, K. M. and Muschenheim, C., Primary cutaneous tuberculosis resulting from mouth-to-mouth respiration. *The New England Journal of Medicine,* Nov. 4, 1965, vol. 273, No. 19, pp. 1035–1036.

Hendricks, A. A. and Shapiro, E. P., Primary herpes simplex infection following mouth-to-mouth resuscitation. *JAMA,* Jan. 18, 1980, vol. 243, No. 3, pp. 257–258.

JAMA. From the Centers for Disease Control and Prevention. Surveillance for occupationally acquired HIV infection–United States, 1981–1992, Dec. 16, 1992, vol. 268, No. 23, p. 3294.

JAMA. Leads from the Morbidity and Mortality Weekly Report. Human immunodeficiency virus infection in the United States. Jan. 22/29, 1988, vol. 259, No. 4, pp. 478–479.

JAMA. From the Centers for Disease Control. HIV seroprevalence among adults treated for cardiac arrest before reaching a medical facility. Jul. 1, 1992, vol. 268, No. 1, pp. 1804–1805.

JAMA. From the Centers for Disease Control. Acquired immunodeficiency syndrome—1991. Aug. 12, 1992, vol. 268, No. 6, pp. 713–714.

(List continued on next page.)

OTHER PUBLICATIONS

Kelen, G. D., et al. Unrecognized human immunodeficiency infection in emergency department patients. *The New England Journal of Medicine*, Jun. 23, 1988, vol. 318, No. 25, pp. 1645–1650.

Lifson, A. R., Do alternate modes of transmission of human immunodeficiency virus exist? *JAMA*, Mar. 4, 1988, vol. 259, pp. 1353–1356.

Loeb, H. S., Cardiac arrest. *JAMA*, May 26, 1975, vol. 232, No. 8, pp. 845–847.

Luce, J. M., et al., New developments in cardiopulmonary resuscitation. *JAMA*, Sep. 19, 1980, vol. 244, No. 12, pp. 1366–1370.

Marty, A. T., Cardiac resuscitation. *JAMA*, Mar. 31, 1975, vol. 231, No. 13, p. 1395.

Myerburg, R. J., et al., Survivors of prehospital cardiac arrest, *JAMA*, Mar. 12, 1982, vol. 247, No. 10, pp. 1485–1490.

Nickalls, R. W. D. and Thomson, C. W., mouth to mask respiration. *British Medical Journal*, May 24, 1986, vol. 292, p. 1350.

Oxer, H. F., Effectiveness of Resuscitation masks as an aid to expired air resuscitation. *The Medical Journal of Australia*, Mar. 16, 1987, vol. 146, p. 332.

Pitchenik, A. E., et al., Acquired immune deficiency syndrome: Evidence for possible transmission by an asymptomatic carrier. *JAMA*, Sep. 9, 1983, vol. 250, No. 10, pp. 1310–1312.

Rawls, W. E., Treatment of herpesvirus infections. *JAMA*, Mar. 29, 1976, vol. 235, No. 13, pp. 1365–1366.

Safar, P., et al., A comparison of the mouth–mouth and mouth-to-airway methods of artificial respiration with the chest–pressure arm–lift methods. *The New England Journal of Medicine*, Apr. 3, 1958, vol. 258, No. 14, pp. 671–677.

Safar, P., Pocket mask for emergency artificial ventilation and oxygen inhalation. *Critical Care Medicine*, Sep.–Oct., 1974, vol. 2, No. 5, pp. 273–276.

Sivaneswaran, N., et al., A new resuscitation mask. *Anesthesia and Intensive Care*. Letter to the editor. Aug., 1986, vol. 12, No. 3, pp. 274–275.

Smith, E. B., Management of herpes simplex infections of the skin. *JAMA*, Apr. 19, 1976, vol. 235, No. 16, pp. 1731–1733.

U.S. Department of Health and Human Services, Centers for Disease Control. *HIV/AIDS Surveillance: U.S. AIDS Cases Reported Through Feb., 1992*, Mar. 1992, pp. 1–18.

U.S. Department of Health and Human Services, Centers for Disease Control. *Understanding AIDS: A Message From the Surgeon General*, HHS Publication No. (CDC) HHS-88-8404, pp. 1–8.

U.S. Department of Health and Human Services, Public Health Service, Centers, for Disease Control. *Protection Against Viral Hepatitis: Recommendations of the Immunization Practices Advisory Committee (ACIP)*. Reprinted from the *Morbidity and Mortality Weekly Report*, Feb. 9, 1990, vol. 39, No. RR-2, pp. 1–26.

U.S. Department of Health and Human Services, Public Health Service, Center for Disease Control. Imunication recommendations for health–care workers. Apr., 1989, pp. 1–8.

Whittenberger, J. L. and Dill, D. B., Editors: Mission accomplished: Successful mouth-to-mouth resuscitation. *Anesthesia and Analgesia*, Jul.–Aug., 1961. vol. 40, No. 4, pp. 440–442. Reprinted from *Artificial Respiration—Theory and Practice*, Paul B. Hoeber, Inc., New York, 1961.

Anne Arundel County (Maryland) Bill No. 17–92 Department of Health, Commissioner of Health, Notice of Public Hearing, Jul. 1, 1992.

Federal Register, vol. 56, No. 235, pp. 64175–64182, Dec. 6, 1991.

"A Safer Mouth-to-Mouth," *USA Today*, p. 3A, Jan. 8, 1992.

"HCL Security Seals Plus," pp. 14–15.

"Rescue with Confidence," 4 pages, Medical Devices International.

Laerdal Pocket Mask with One-Way Valve," 2 pages, Laerdal Medical Corporation.

"Respironics Seal Easy® Resuscitation Mask," 11 pages, Respironics Inc.

EMERGENCY CPR MASK STATION

This application is a continuation of U.S. application Ser. No. 07/878,261, filed May 4, 1992, now abandoned.

BACKGROUND OF THE INVENTION

The present invention relates to equipment and methods for administering cardiopulmonary resuscitation (CPR). It more particularly relates to emergency administration of mouth-to-mouth resuscitation to patients or victims in public areas or in various locations within an employer's work site.

In performing CPR on patients or victims, there is a possibility that the attendant or rescuer can contract one or more serious communicable diseases or viruses. These diseases and viruses include the Hepatitis "B" virus and the human immunodeficiency virus (H/V) which can lead to the development of acquired immunodeficiency syndrome (AIDS). According to an Alabama study reported in a very recent issue of the *American Journal of Public Health*, the Hepatitis "B" virus, which can be fatal, is not only more prevalent but is more easily transmitted (from patient to dentist) than is the AIDS virus. These viruses can be spread from the victim to the rescuer via the victim's blood or other bodily fluids. Blood, though not immediately visible, may be present in the victim's saliva due to a facial injury, for example.

To prevent the transmission of the virus through the area of the mouth of the rescuer, protective masks are often used, most having one-way valves. Examples of such masks are those shown in U.S. Pat. Nos. 3,625,351, 4,944,291, 5,020,529, 3,802,428, 4,819,628, 4,856,506 and 4,697,587. (These and each of the other patents and publications mentioned anywhere in this disclosure are hereby incorporated by reference in their entireties.) Since the diseases can also be transmitted through the skin, protective (e.g., latex, vinyl) gloves should be worn by the person or persons carrying out the resuscitation. The gloves protect the rescuer's hands, especially when clearing a victim's throat of obstructions.

Unfortunately, when CPR or mouth-to-mouth resuscitation is needed or required, these masks and gloves are often not available. This has two unfortunate consequences. First, the potential rescuer may choose not to even attempt CPR or mouth-to-mouth resuscitation for fear of contracting a potentially deadly disease. Since time is of the essence and a willing rescuer is often not immediately available, the victim may then die of the potential rescuer chooses not to administer CPR. Second, if the victim in fact does have such disease then the rescuer may contract the disease and may subsequently become very ill or even die, and/or may infect someone else. It is also possible that the disease could be transmitted from the rescuer to the victim.

Since as a practical matter it is not possible for everyone to carry on his person masks and gloves, a serious problem and concern has developed. In fact, as reported on page 3A of the Jan. 8, 1992 issue of *USA Today*, New York City has enacted a law requiring public facilities to have available masks with one-way valves. Additionally, recent OSHA legislation, Standard 29 CFR Part 1910.1030, published in the *Federal Register* of Dec. 6, 1991, addresses an employer's responsibility in protecting employees from bloodborne pathogens during emergencies.

These disadvantages and problems could be overcome if there were a ready, convenient and dependable supply of masks and gloves in most if not all public areas and in populated areas of an employer's physical plant.

SUMMARY OF THE INVENTION

Accordingly, primary objects of the present invention are to provide a system for increasing the likelihood that a potential rescuer will administer CPR on a victim needing it and that such administration is less likely to result in the transmission of viruses or other diseases.

Directed to achieving these objects, a novel emergency CPR station and process for using same are herein provided. This station includes a cabinet mounted to a wall in an exposed position and in an area likely to be frequented. The cabinet has a piezo buzzer mounted on top of it, a door hinged to one side and a storage area defined inside. Two CPR masks are stored in the cabinet generally adjacent the back wall thereof, and four pairs of non-sterile latex hypoallergenic gloves are hung in a bag from the back of the cabinet door. With the cabinet stocked with one or more masks and the gloves, the door is closed and a plastic tie seal is attached through holes in the door and the sidewall of the cabinet, thereby sealing the door closed. In the event of an emergency requiting the use of the mask and/or gloves, the plastic seal is broken by the rescuer by pulling and twisting the seal, and thereby allowing the door to open. As the door opens an electrical circuit, powered by a nine volt dry cell battery and wired to the alarm or buzzer, is activated and the alarm is thereby audibly energized. With the door open the mask and gloves can thereby be easily removed from the cabinet and used in the CPR procedure. The alarm continues to sound thereby alerting everyone in the vicinity to this emergency event. Those alerted can assist the rescuer in any number of ways, including relieving him as needed, assisting in the CPR technique, administering aid to others who may need it or calling an ambulance or other professional medical assistance.

The cabinet is mounted on a wall such that the door with an attached ceramic doorknob, by its own weight, remains open and does not close thereby shutting off the alarm. The alarm, however, can be mined off using a key in a key-actuated lock switch on the fight side of the cabinet. After the mask(s) and/or gloves have been removed, they can easily be replaced by authorized persons, the door then closed and a new plastic seal attached to it. This sealing arrangement allows one to readily determine by the absence of a seal and/or by the presence of a broken seal whether the cabinet is likely to be stocked. Since the seal is also a separate item from the cabinet including the cabinet door, the breaking or removal thereof does not damage the cabinet and the seal replacement is very easy.

Other objects and advantages of the present invention will become more apparent to those persons having ordinary skill in the art to which the present invention pertains from the foregoing description taken in conjunction with the accompanying drawings.

DETAILED DESCRIPTION OF PREFERRED EMBODIMENTS

Figure 1:
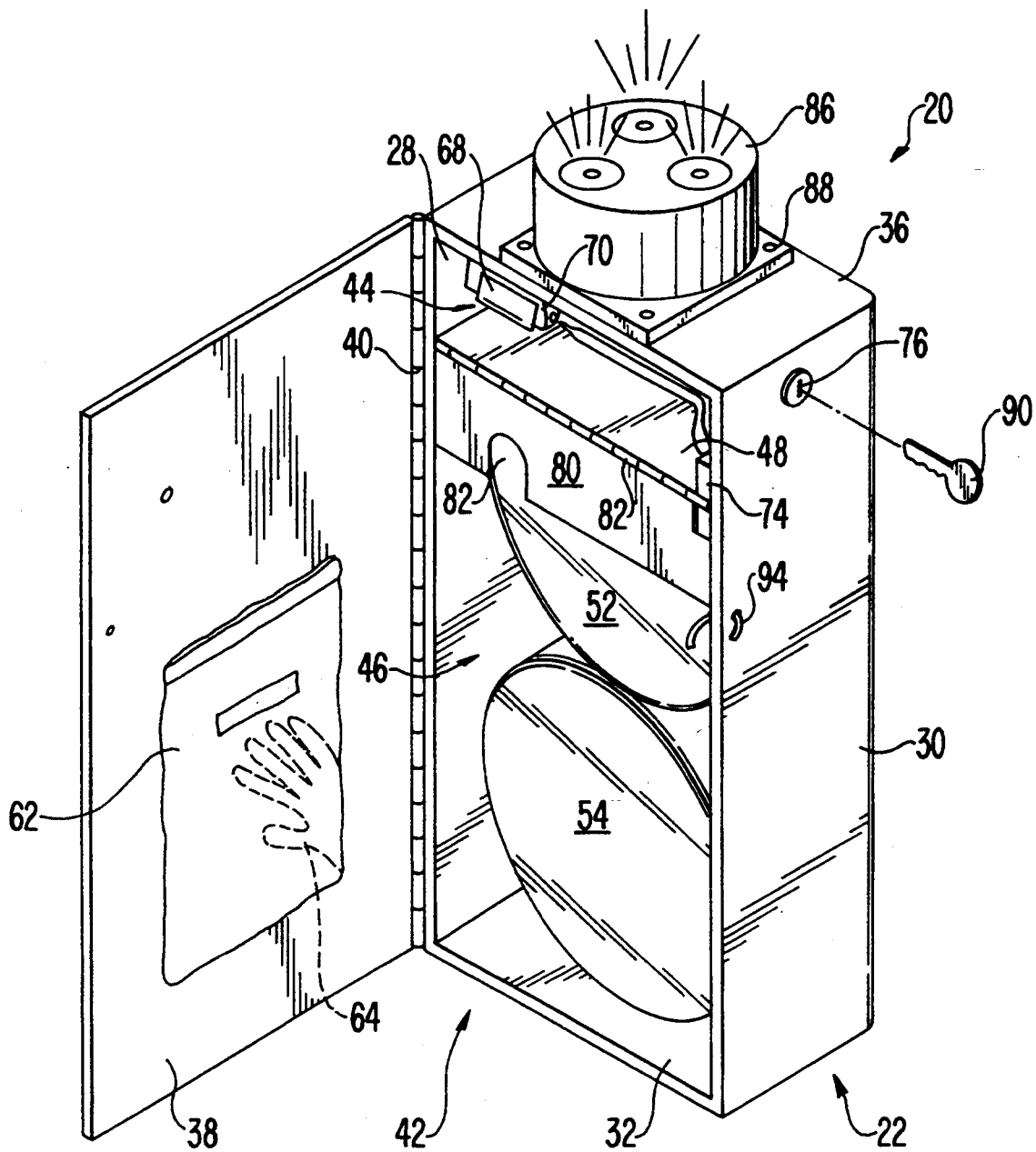
FIG. 1 is a perspective view of an emergency CPR station of the present invention illustrated in an opened, alarm activated condition.

Referring to the drawings, an emergency CPR station of the present invention is illustrated generally at 20. The station 20 includes a cabinet shown generally at 22 which can be fastened to a wall in a public area by four screws. Such public areas can include hospitals, medical centers, shopping malls, large industrial and governmental buildings, hotels and amusement parks. The cabinet 22 is preferably mounted against a flat wall surface and not in the recess of the wall, so the cabinet is thereby fully visible on a three sides. The cabinet 22 has a box-like configuration and is preferably constructed of one-quarter inch, polycarbonate plastic approximately International Blue. This bright blue color is preferred since it is generally associated with respiratory care equipment. The cabinet 22 measures in a preferred embodiment approximately 15 × 16¾ × ¾ inches. It is constructed of a pair of sidewalls 28, 30, a floor 32, a back wall 34, a top wall 36 and a door 38. The door 38 also constructed of this blue plastic is affixed with a piano hinge 40 approximating the length of the sidewall and cemented in place thereto so that the door can swing from left to right.

When the door 38 is open as illustrated in FIG. 1, the interior shown generally at 42 of the cabinet 22 is readily visible and its contents are accessible. The interior 42 is divided into upper and lower sections or compartments 44, 46, separated by a plastic shelf 48. The shelf 48 is approximately two inches wide and extends the entire width of the cabinet 22 and is also cemented in place to the cabinet side and back walls 28, 30, 34. While the upper compartment 44 has a height of only approximately two and a half inches, the bottom, much larger, compartment 46 has a height of approximately thirteen inches.

The bottom compartment 46 provides the storage area for a pair of CPR masks 52, 54, disposed or suspended one above the other. Each of the masks 52, 54 is held in the bottom compartment 46 with one inch strips of a hook and loop fastener 56, 58, sold under the trademark "VELCRO". The VELCRO strip 56 (or 58) allows for the easy release and removal of the mask 52 (or 54). In other words, the VELCRO strips 56, 58 loosely hold the masks 52, 54 in the bottom compartment 46 such that with the door 38 open the masks do not freely fall out of the cabinet interior 42 while ready access and removal of the masks is provided.

Each of the CPR masks 52, 54 can be contained in its own plastic see-through case, such as that of the "SEALEASY" Resuscitation Mask, available from Respironics Inc. of Monroeville, Pa. Alternative masks include the "Laerdal POCKET MASK" (with a one-way valve), Cat. No. 820003, available from Laerdal Medical Corp., of Armonk, NY, and the "CPR MICROSHIELD Clear Mouth Barrier" (U.S. Pat. No. 4,819,628) from Medical Devices International of Curnee, IL. They also or alternatively can be one or more of the CPR masks mentioned in the Background of the Invention portion of this disclosure. Each mask 52 or 54 is thus held in place by VELCRO strips 56 or 58 that are positioned on the upper and lower back walls, respectively, of the cabinet 22. Removal of either mask 52, 54 from the cabinet interior 42 is accomplished by simply grasping the mask case and pulling it away from the VELCRO strips 56, 58. An alternative method of releasably securing the masks 52, 54 in the lower compartment 46 is by using coil springs attached to and extending across the width of the compartment in front of the masks. The masks are simply grasped and pulled down and under the springs to remove them from the cabinet interior.

A plastic bag 62 containing four pairs of non-sterile latex hypoallergenic gloves 64, such as those available from Foster Medical Supply of Baltimore, MD, is attached to the backside of the cabinet door 38 with a one inch strip of Velcro. In an emergency, the entire bag 62 can be pulled away from and off of the door 38 and taken to the scene of the emergency, along with the CPR mask(s) 52 and/or 54. It is also within the scope of this invention to store impervious gowns, face shields and/or other CPR or emergency equipment (not shown) in the cabinet interior 42. The gowns, for example, could be stored in the present cabinet by placing several in a plastic bag and mounting them on the inside of the door 38 with VELCRO strips (56, 58) in the same fashion as the latex gloves.

Within the upper compartment 44 is a nine-Volt dry cell battery 68 mounted in the cabinet 22 by a U-shaped metal clip 70 and fastened with a screw to the floor of the upper compartment 44. As pictured in FIG. 1, the clip 70 and battery 68 can be positioned in the upper left corner of the compartment 44 to conserve space and to keep the wiring in order. A lever switch 74 with associated wiring is fastened to the right sidewall 30 of the cabinet 22 with two screws, approximately two inches from the top edge thereof. A key switch 76 is attached midway of the upper right side approximately one inch from the top edge and with its associated wiring. A complete roller catch is arranged midway on the under side of the top wall 36, is held in place by a pair of screws and secures the upper compartment door 80 to the edge of top wall 36. The upper compartment 44 can be closed by a door 80, closing upwardly about a piano hinge 82 extending horizontally the width of the front edge of the shelf 48 and cemented thereto. On the upper left side of the door 80, approximately one inch from the left edge thereof, is a U-shaped hole 82, as shown in FIG. 1. The hole 82 permits easy access to the upper compartment 44 by the user inserting a finger therein and then pulling the door 80 forward and thereby open.

Figure 2:
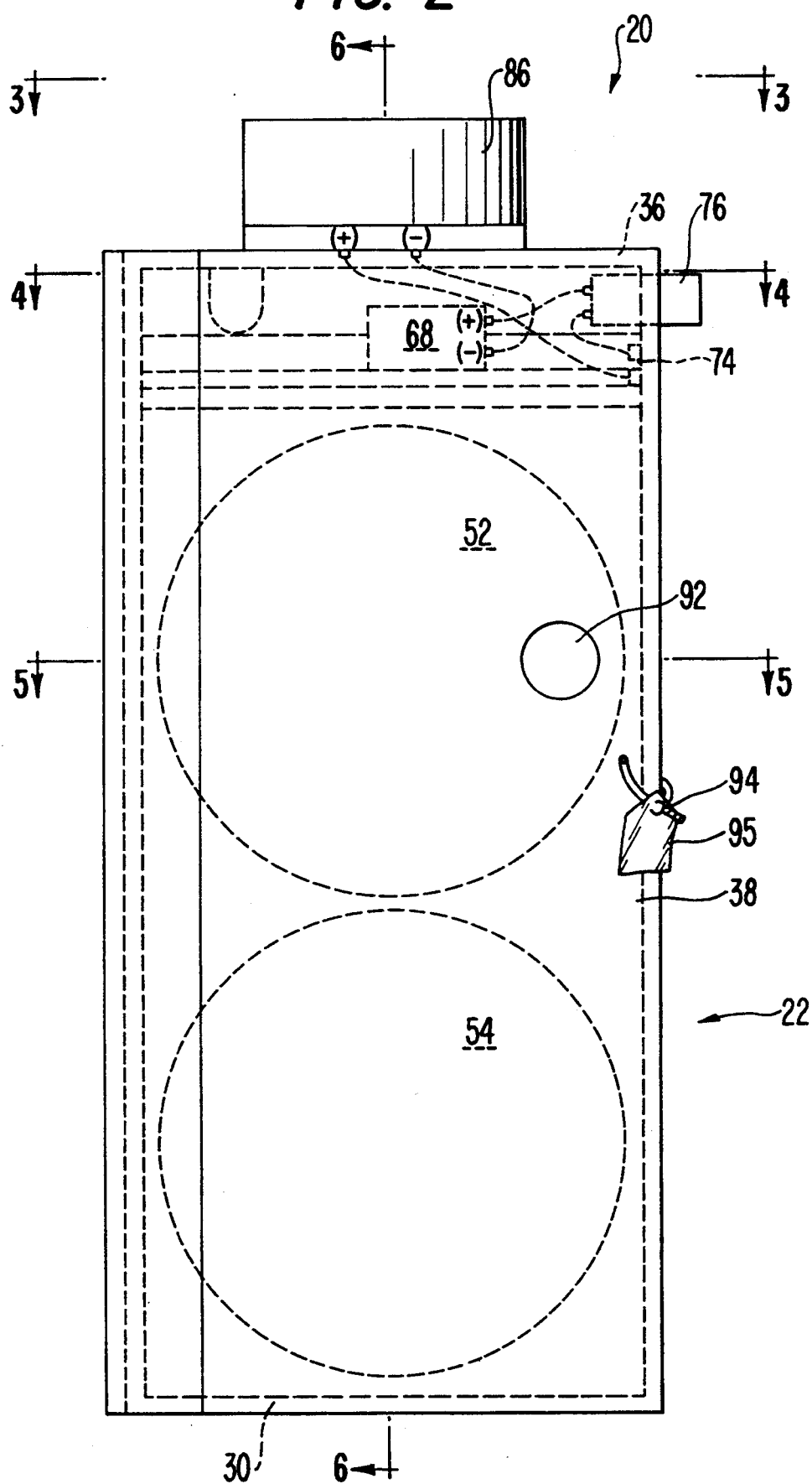
FIG. 2 is a side elevational view of the station of FIG. 1 illustrated in a door closed and sealed condition.
Figure 3:
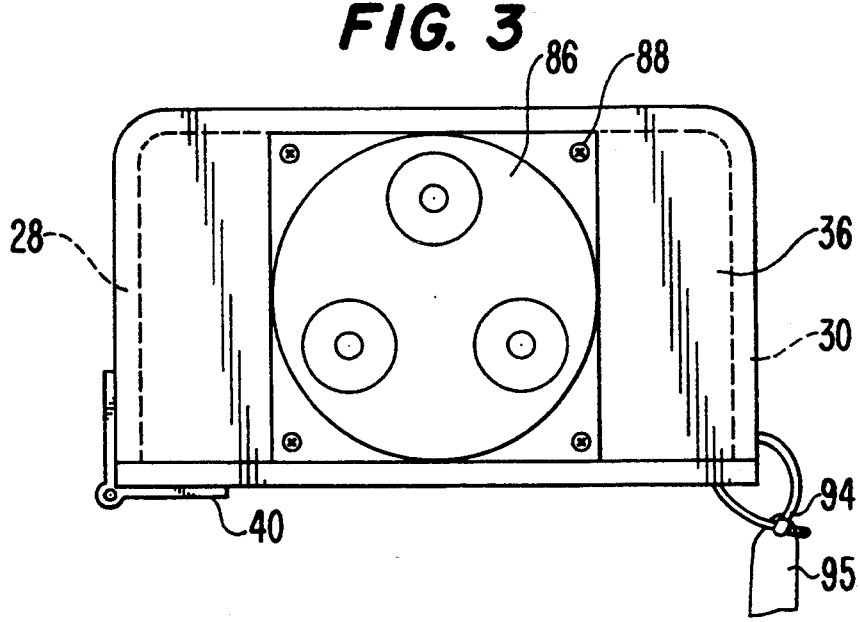
FIG. 3 is a top plan view taken on line 3—3 of FIG. 2.
Figure 4:
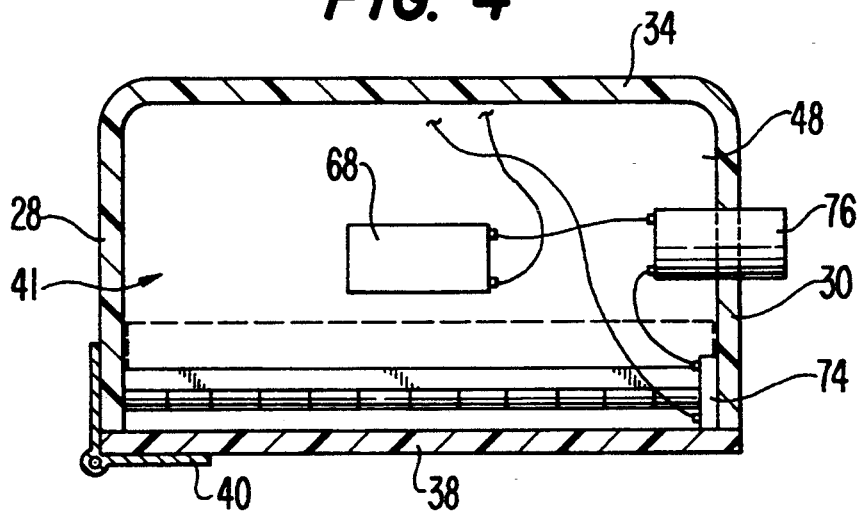
FIG. 4 is a cross-sectional view taken on line 4—4 of FIG. 2.
Figure 5:
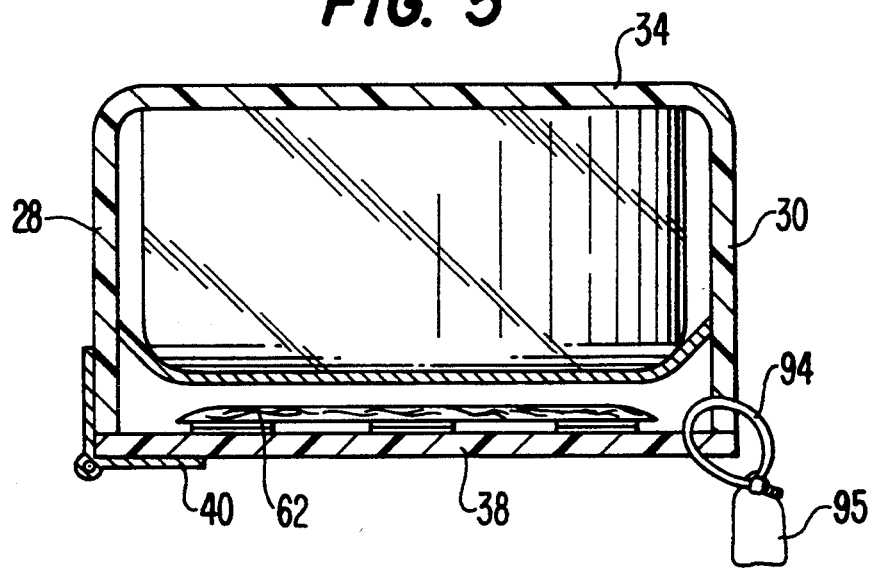
FIG. 5 is a cross-sectional view taken on line 5—5 of FIG. 2.
Figure 7:
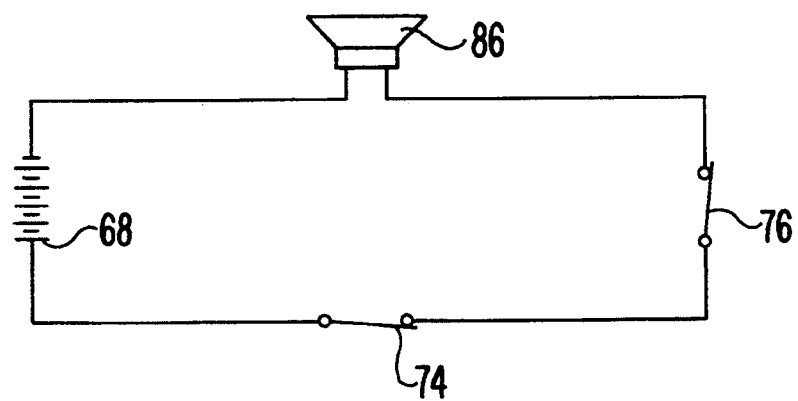
FIG. 7 is a schematic view of the alarm electrical circuit of the station of FIG. 1.

On the center of the top wall 36 of the cabinet 22 is mounted a piezo buzzer 86, measuring approximately 3½ × 3½ inches and secured thereto by four screws 88. These screws 88 can be tamperproof screws with countersunk heads to reduce the likelihood of vandalism to the buzzer 86. An example of a suitable buzzer 86 is the "ICC" buzzer available from Allied Electronics, of Columbia, MD. It is rated at one hundred and fifteen decibels, has a six to fifteen voltage range, and its wiring can be fed through a hole in the top wall 36 into the upper compartment 44 to the battery switch circuit as seen in FIGS. 2 and 7. In lieu of or in addition to the buzzer 86, a strobe or revolving light (not shown) can be used. Examples of other types of article removal signaling devices are shown in U.S. Pat. Nos. 2,683,260 and 1,178,719.

A white ceramic knob 92 is attached by a screw to the outside surface of the cabinet door 28 approximately two inches below the top edge thereof and an inch away from the upper right edge. A plastic seal 94, having a seal tab 95, is positioned below the door knob 92 and extends through a 9/32 inch hole on the right sidewall 30 of the cabinet 22 and through another 9/32 inch hole drilled in the door 38 itself. This seal 94 can be, for example, the "HCL Security Seal" which is available from Health Care Logistics, Inc. of Ohio.

To gain access to the cabinet interior 42 and its contents and thereby simultaneously energize the piezo buzzer 86, the plastic seal 94 is broken (as depicted in FIG. 1) by pulling down on it to the left or right and at the same time twisting it. This seal 94 is advantageous in that the act of breaking it does not damage any other component of the station 20 including any portion of the cabinet door 38. It also does not result in broken glass which could injure the rescuer and/or victim and may even produce cuts thereby increasing the likelihood of disease transmission. Examples of other types of cabinets for different uses are shown in U.S. Pat. Nos. 4,449,588, 3,067,822, 4,109,985, 3,042,910, 4,015,250 and 4,763,732.

When the door 22 opens the normally open lever switch 74 is closed thereby completing the circuit and energizing the buzzer 86 through the battery 68. To turn this loud buzzer 86 off via the switch 74 requires that constant pressure be applied to the switch. This is advantageous since it is not desirable to have the buzzer 86 turned off as long as the emergency CPR event is taking place since the buzzer continually alerts those in the vicinity to the emergency. This could, for example, assist the emergency medical personnel summoned to quickly locate the victim.

The buzzer 86 can be deactivated, however, by inserting a key 90, which ideally would be available only to authorized persons, into the key switch 76 provided on the right sidewall 30 of the cabinet 22 and then turning the key to the left. With the door 38 secured by the seal 94 and the key turned one position to the right activated to the "on" position, the key switch 76 will automatically be in an open or "on" status and ready to be utilized in an emergency. The piezo buzzer 86 can be tested for proper operation by turning the key switch 76 one more position to the right to the "test mode" which activates the piezo buzzer to ensure proper operation, as long as the key is manually held in the "test mode." Once released, the key will revert back to the "on" position and can be removed. An example of a suitable key switch 76 is the "C & K" switch available from C & K Components, Inc. of Newton, Mass.

Following the emergency event it is of course desirable to restock the emergency CPR station 20. This is a simple procedure whereby an authorized person inserts the necessary replacement CPR gloves 64 and/or masks 52, 54 in the cabinet interior 46, closes the cabinet door 38 and inserts a new plastic seal 94 through the holes, securing the lock in place by pulling the end of the seal through the hole in the tab until tight. Since this restocking is done by authorized persons, it is readily apparent by simply looking at the cabinet 22 whether it has been restocked since the seal 94 will be in place and unbroken.

Figure 6:
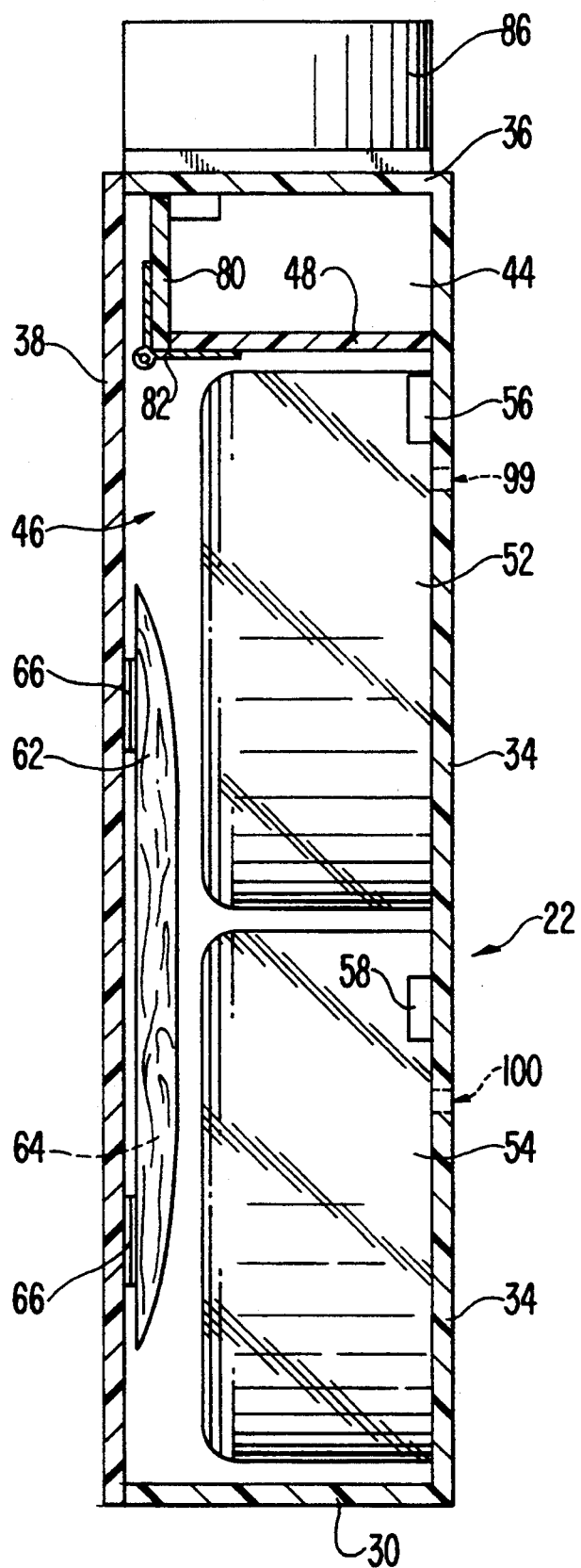
FIG. 6 is a cross-sectional view taken on line 6—6 of FIG. 2.
Figure 8:
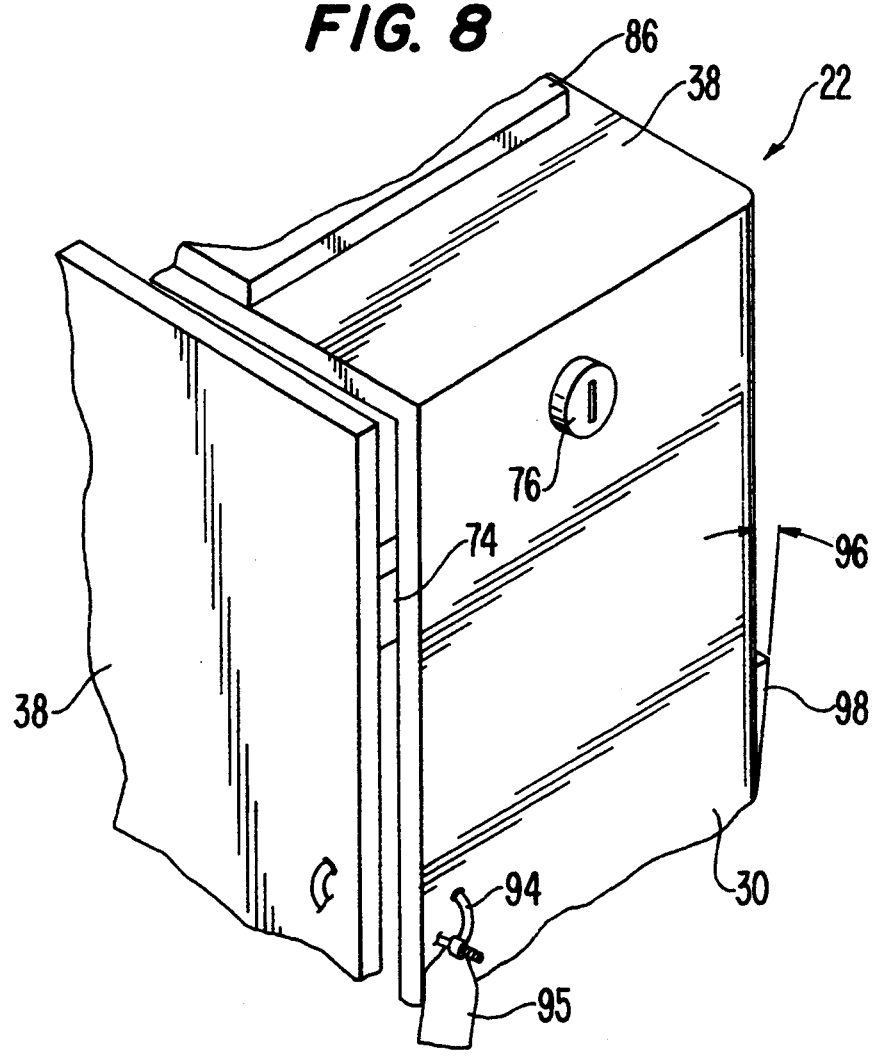
FIG. 8 is a perspective view of a top corner of the station of FIG. 1 illustrating a wall mounting thereof.

The door 38 by its own weight and with the seal 94 broken will hang in an open position and not in a closed position thereby closing the lever switch 74. In fact, the lever switch 74 itself can provide a biasing function for biasing the door 38 away from a closed position. Referring to FIG. 8, a further arrangement of the present invention for ensuring that the door 38 does not assume a natural closed position is to mount the cabinet 22 against the wall at a slight forward tilt or angle 96. For this arrangement a 2"×6"×⅛ polycarbonate plastic strip 98 can be affixed over the area where the top two mounting screws are located on the back of the cabinet 22. This plastic strip 98 is glued centered over the (two) holes 99, as shown in FIG. 6, which are one-quarter inch holes, positioned four inches from the top edge and spaced two inches from the outer edge. Similarly, one-quarter inch mounting holes 100 are positioned at a lower location on the back wall, four inches from the bottom edge and two inches from the outer edge, and are provided for additional strength and support when mounted in place. This provides the slight downward tilt or angle 96 in the area where the cabinet 22 is mounted thereby removing the possibility that the unsealed door 38 will close by itself. As previously mentioned, the placement of the lever switch 74 on the upper right edge of the cabinet wall also provides pressure against the edge of the door 38 to prevent it from fully closing and remaining closed after the seal 94 has been broken.

Testing of the battery 70 and the piezo buzzer 86 can be accomplished by intentionally breaking the plastic seal 94 to activate and/or by inserting key 90 into key switch 76 and making one clockwise turn to the right to the "test" position. The (nine Volt) battery 70 should also be routinely changed at least every three months and after each emergency to ensure adequate available operating power. In addition, testing/inspection of the mask station 20 should be carded out periodically, at least once per month, for example. This inspection can be noted with the inspector's initials, the date, and the action taken on the inspection stickers provided and affixed to the inside of the main door 38, below the package of latex gloves.

From the foregoing description, it will be evident that there are a number of changes, adaptations and modifications of the present invention which come within the province of those skilled in the prior art. However, it is intended that all such variations not departing from the spirit of the invention be considered as within the scope therein as limited solely by the claims appended hereto.

What is claimed is:

1. An emergency cardiopulmonary resuscitation (CPR) station, comprising:

a CPR equipment cabinet including a cabinet top wall, a cabinet bottom wall, a plurality of cabinet side walls, and a cabinet door;

said cabinet top wall, said cabinet bottom wall, said plurality of cabinet side walls, and said cabinet door together defining a cabinet interior, said cabinet door being movable between a closed position wherein access to said cabinet interior is blocked and an open position wherein access to said cabinet interior is provided, said cabinet interior including an upper compartment and a lower compartment disposed therebelow;

at least one CPR mask provided within said cabinet interior, said at least one CPR mask disposed in said lower compartment, mask attachment means affixed to at least one of said plurality of cabinet side walls, said mask attachment means releasably securing said at least one CPR mask to at least one of said plurality of cabinet side walls;

at least one pair of latex gloves provided within said cabinet interior, said latex gloves disposed within a plastic bag, glove attachment means affixed to said cabinet door, said glove attachment means releasably securing said plastic bag to said cabinet door, said plastic bag and said latex gloves thus disposed within said cabinet interior when said cabinet door is in said closed position;

an alarm mounted to and on top of said cabinet top wall, said alarm disposed outside of said cabinet interior;

a switch assembly including a battery disposed in said upper compartment, said switch assembly operatively connected to said alarm, said switch assembly actuating said alarm when said cabinet door is in said open position;

a manually operable switch operatively connected to said switch assembly, said manually operable switch being connected to deactivate said alarm responsive to said cabinet door being in said open position;

at least one aperture in said cabinet door and at least one aperture in one of said plurality of cabinet side walls;

a sealing element, said sealing element received in said at least one aperture in said cabinet door, said sealing element also received in said at least one aperture in one of said plurality of cabinet side walls, said sealing element movable between an unsealed position and a sealed position, said sealing element in said sealed position maintaining said cabinet door in said closed position and said sealing element in said unsealed position allowing said cabinet door to be moved to said open position, said sealing element thereby allowing said switch assembly to automatically actuate said alarm when said cabinet door is moved to said open position;

mounting means for mounting said equipment cabinet to a wall surface such that said equipment cabinet is disposed at a slight angle with respect to said wall surface whereby said cabinet door is biased into said open position when said sealing element is in said unsealed position.

2. An emergency cardiopulmonary resuscitation (CPR) station as in claim 1 wherein said switch assembly comprises a lever switch attached to said equipment cabinet, said lever switch disposed in operative relation to said cabinet door such that said lever switch automatically activates said alarm when said cabinet door is moved from said closed position to said open position.

3. An emergency cardiopulmonary resuscitation (CPR) station as in claim 1 wherein said mask attachment means comprises at least one hook and loop fastener strip.

4. An emergency cardiopulmonary resuscitation (CPR) station as in claim 1 wherein said glove attachment means comprises at least one hook and loop fastener strip.

5. An emergency cardiopulmonary resuscitation (CPR) station as in claim 1 wherein said sealing element comprises a plastic tie device.

6. An emergency cardiopulmonary resuscitation (CPR) station as in claim 1 further comprising mounting means for mounting said CPR equipment cabinet to a flat wall surface of a wall such that said CPR equipment cabinet extends out a distance from the wall in a visible exposed position.

7. An emergency cardiopulmonary resuscitation (CPR) station as in claim 1 wherein said manually operable switch includes a key separable from said CPR equipment cabinet.

8. An emergency cardiopulmonary resuscitation (CPR) station as in claim 1 wherein said manually operable switch is disposed such that said manually operable switch may be accessed from outside said CPR equipment cabinet interior.

9. An emergency cardiopulmonary resuscitation (CPR) station as in claim 1 wherein said alarm comprises a piezo buzzer disposed on said top wall of said CPR equipment cabinet.

10. An emergency cardiopulmonary resuscitation (CPR) station as in claim 1 further comprising an upper compartment door generally in said cabinet interior, said upper compartment door being movable between open and closed positions relative to said upper compartment.

11. An emergency cardiopulmonary resuscitation (CPR) station as in claim 10 wherein said upper and lower compartments of said CPR equipment cabinet are separated by a cabinet shelf.

12. An emergency cardiopulmonary resuscitation (CPR) station as in claim 11 wherein said cabinet shelf includes a front edge and said upper compartment door includes a door hinge connected to and extending along said front edge.

* * * * *